United States Patent [19]

Ayres

[11] 3,957,654

[45] May 18, 1976

[54] PLASMA SEPARATOR WITH BARRIER TO EJECT SEALANT

[75] Inventor: Waldemar A. Ayres, Sun City, Ariz.

[73] Assignee: Becton, Dickinson and Company, East Rutherford, N.J.

[22] Filed: June 5, 1975

[21] Appl. No.: 583,955

Related U.S. Application Data

[63] Continuation-in-part of Ser. No. 446,361, Feb. 27, 1974, abandoned.

[52] U.S. Cl. .......................... 210/516; 23/258.5 R; 128/272; 210/DIG. 23; 233/1 A; 233/26
[51] Int. Cl.² ......................................... B01D 21/26
[58] Field of Search .......... 23/230 B, 258.5, 259 R, 23/292; 128/2 F, 214 R, 218 M, 272, DIG. 5; 210/83, 84, 514–518, DIG. 23, DIG. 24; 233/1 A, 1 R, 26

[56] References Cited
UNITED STATES PATENTS

| | | | |
|---|---|---|---|
| 3,780,935 | 12/1973 | Lukacs et al. | 210/83 X |
| 3,852,194 | 12/1974 | Zine, Jr. | 210/83 |

*Primary Examiner*—John Adee
*Assistant Examiner*—Robert G. Mukai
*Attorney, Agent, or Firm*—Kane, Dalsimer, Kane, Sullivan and Kurucz

[57] ABSTRACT

A blood collection and separator assembly capable of separating blood into its component parts of plasma or serum, the light phase, and cellular portion, the heavy phase, is disclosed. The assembly comprises a container having one open end for receiving blood and a two part barrier assembly slidably disposed in the container. The outer part or shell of the latter assembly has a specific gravity greater than the light phase of blood and the inner part or plunger has a specific gravity less than the heavy phase of blood. Interposed between the two parts is a viscous sealant, such as silicone grease. After the blood separates into its light phase and heavy phase under centrifugal force, the barrier assembly is introduced so it sinks to the interface between separated phases. Upon applying further centrifugal force, the inner plunger tends to move upward while the outer shell tends to move downward thus causing a squeezing action on the interposed sealant. This forces the sealant out through ports in the outer shell where it produces a circular impervious barrier between the barrier assembly and the inner walls of the container.

5 Claims, 3 Drawing Figures

PLASMA SEPARATOR WITH BARRIER TO EJECT SEALANT

CROSS REFERENCE TO RELATED APPLICATIONS

This application is a Continuation-in-Part of Application Ser. No. 446,361 filed Feb. 27, 1974, and now abandoned.

BACKGROUND OF THE INVENTION

1. Field of the Invention

The invention concerns an assembly for the separation of blood into its component light liquid and heavy, substantially cellular phases under centrifugal force.

2. Brief Description of the Prior Art

It is known to separate blood into its component parts by centrifugation, for example, the assembly disclosed in U.S. Pat. No. 2,460,641. However, this particular assembly does not employ a means for sealing the separated plasma or serum phase from the cellular phase.

It is also known to provide assemblies for manually separating the plasma or serum phase from the cellular phase, for example, as disclosed in U.S. Pat. Nos. 3,586,064; 3,661,265; 3,355,098; 3,481,477; 3,512,940; and 3,693,804. In all of these devices the serum is collected in a blood collection container and means are provided for separating the plasma or serum phase from the cellular phase employing filters, valves, transfer tubes or the like.

It is also known to provide assemblies for the sealed separation of blood in which a piston is actuated by centrifugal force such as is disclosed in U.S. Pat. Nos. 3,508,653 and 3,779,383. These devices use either a compressible piston made of resilient material or valve means associated with the piston to effect a sealed separation after centrifugation. It is also known that a liquid sealant can be used for the separated portions of a blood sample as is covered by U.S. Pat. No. 3,780,935, but such patent does not disclose the piston for squeezing out the sealant of the present invention.

SUMMARY OF THE INVENTION

It is an object of the present invention to provide a serum/plasma separator assembly including a collection container and a two part barrier assembly slidably disposed in the container, which barrier is adapted, when the blood is centrifuged, to squeeze out a sealant and form a seal at approximately the plasma/serum-cellular interface.

It is another object of the invention to provide a serum/plasma separator assembly which is economical to manufacture and can be used in conjuction with standard blood collecting equipment.

DESCRIPTION OF THE PREFERRED EMBODIMENTS

Figure 1:
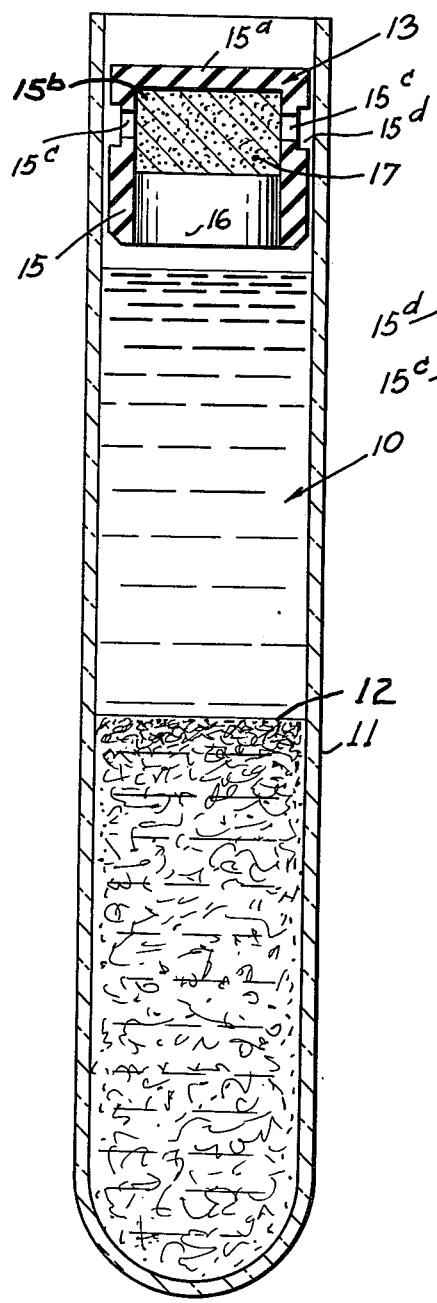
FIG. 1 is a sectional, elevational view showing the plasma/serum separator assembly of the present invention and illustrating the two part barrier assembly containing sealant inserted into the container after the blood has been first centrifuged and separated into its two phases.
Figure 3:
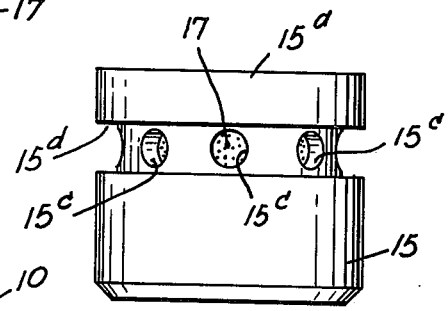
FIG. 3 is a side view of the barrier assembly showing the outer shell and the ports through which the sealant is ejected.
Figure 2:
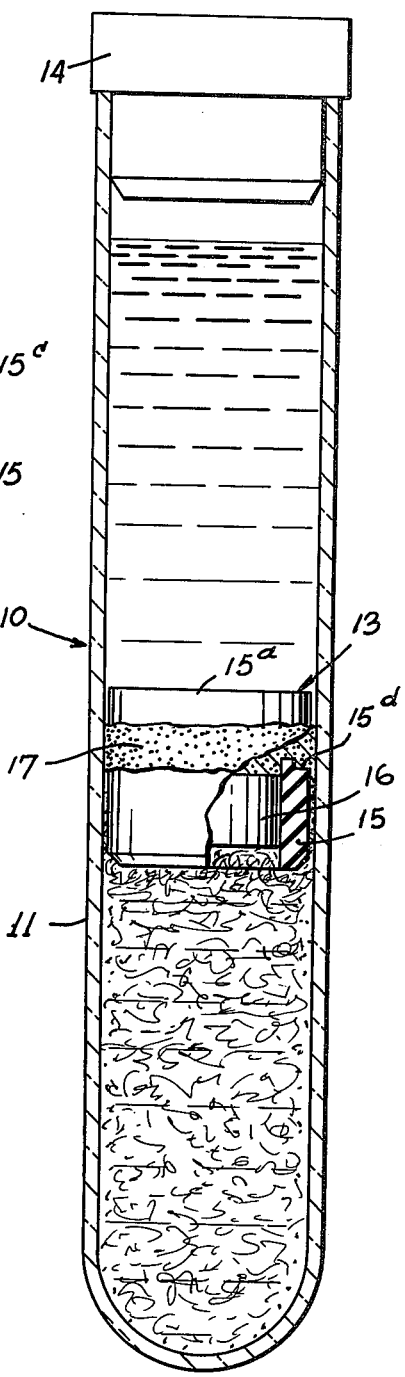
FIG. 2 is a sectional, elevational view similar to the view of FIG. 1, showing the barrier assembly and the sealant forming an impervious barrier across the container slightly above the plasma/serum cellular interface.

For a better understanding of the invention, a description of the drawings of the illustrative embodiments shown in FIGS. 1-3 follows.

In FIG. 1 the separator assembly 10 comprises a tubular member or container 11 which is preferably made of glass but also of any other material conventionally used to fabricate laboratory vessels. The container 11 has been filled with blood and centrifuged to separate the blood into its two phases, the light phase (plasma or serum) being in the upper portion of the container and the heavy phase (substantially cellular material) occupying the lower portion of the container 11. The line of separation between the two separate phases constitutes the interface 12 as shown in FIG. 1.

The barrier assembly 13 of the present invention is inserted into the container 11 after separation of the blood components, as shown in FIG. 1 and a closure member 14 is then preferably inserted into the container to seal the open end (not shown in FIG. 1). Barrier assembly 13 has a diameter less than the inside diameter of container 11 so that it is loosely disposed in the container. Advantageously the difference in diameters is 2 to 3 thousandths of an inch, but this is not critical.

Closure member 14 (FIG. 2) is preferably made of elastomeric material capable of being penetrated by a cannula so that blood can be transferred from a blood source into the container 11 under aseptic conditions and light phase withdrawn from the container 11 after operation of assembly 10. The closure 14 should be self-sealing so that when the cannula is removed from the closure 14 there will be no loss of blood passing through the penetration portion of the closure. After insertion of the barrier assembly 13 into the container and sealing of such container, the filled assembly is centrifuged to emplace a sealing barrier at the approximate position of the interface between separated blood phases as seen in FIG. 2.

The barrier assembly 13 is formed of an outer shell 15 having a top portion 15a and a cavity 15b within the shell. The upper part of the shell 15 is provided with ports 15c extending from the cavity to the outside of the shell. As shown best in FIG. 3, ports 15c are placed on the periphery of shell 15 beneath portion 15a and within annular channel 15d of the sidewall of barrier assembly 13. A plunger 16 is adapted to fit into the cavity of the shell, such plunger 16 being shorter than the depth of the cavity to provide space in the cavity for a sealant 17, such as silicone grease. The specific gravity of the sealant 17 employed in the assembly 10 is not a critical feature but advantageously is within the range of from 1.03 to 1.09. The sealant 17 should have a consistency such that it will not ooze from its position in the cavity 15b until a force is exerted upon it. Illustrative of such a consistency is that which is shown by the consistency of unworked petroleum jelly (150 to 190; cone penetration ASTM test method D-217) and of unworked stopcock grease (190 to 220; cone penetration ASTM test method D-217). The specific gravity of the shell 15 is more than the specific gravity of the light phase of blood (1.03) but less than the specific gravity of the substantially cellular phase of the blood (1.09). The specific gravity of plunger 16 is within the range of from 1.02 to 1.08 but is less dense than shell 15 so it will have an upward movement in relation to shell 15, during centrifugation. The average specific gravity of the entire assembly 13 including sealant 17 is between 1.03 to 1.09, preferably 1.06.

When the container 11 containing the two separated blood phases and the barrier assembly 13 including sealant 17 are centrifuged, the loosely disposed barrier assembly 13 first descends to the interface 12 and floats there. Under continued centrifugal force the relatively less dense plunger 16 tries to move upwardly while the relatively more dense shell 15 tries to move downwardly, thus creating a squeezing action between the two parts. The sealant 17 in the cavity 15b is thus put under squeezing pressure which forces the sealant 17 out through the ports 15c filling the annular channel 15d outside the ports. The sealant 17 thereby produces a circular seal between the barrier assembly 13 and the inner wall surface of the container 11, thus providing an impervious barrier slightly above the interface 12, between the two separated blood phases as shown in FIG. 2.

After centrifugation has been terminated the separated blood sample is ready for use and the desired serum or plasma may be withdrawn as previously described. Prior to withdrawal, the assembly may be handled, shipped, etc. without remixing the separated phases. While variations of the invention herein may be had, the objectives of the invention have been illustrated and described.

What is claimed:

1. A separator assembly, capable of separating blood into its component parts of plasma or serum and cellular portion comprising:
   a. a tubular container having an open end which is adapted to receive blood to be separated into a light and a heavy phase;
   b. a barrier assembly insertable into the container after contained blood has been separated into its light and heavy phases said barrier assembly having a diameter less than the inside diameter of said container;
   c. said barrier assembly comprising an outer shell closed at the top and defining a cavity within the shell, a plurality of ports extending from the upper portion of the cavity to the outside of the shell, a plunger fitted into and closing the lower end of the cavity with space between the top of the plunger and the upper portion of the cavity, and a sealant inserted into the space in the cavity, said sealant having a consistency selected such that it will be ejected from the ports when the plunger moves upwardly into the cavity;
   d. said shell of the barrier assembly having a specific gravity between 1.03 and 1.09, and said plunger having a specific gravity of from 1.02 to 1.08 provided the density of the plunger is less than the density of said shell and the average specific gravity of the entire barrier assembly is between 1.03 and 1.09; whereby when the barrier assembly is inserted into the separated blood held within said container it will descend to the interface between the light and heavy phase and upon centrifugation the plunger will move into said cavity, thereby to squeeze the sealant within said cavity and cause it to eject through said ports to form a circular seal between the barrier assembly and the inner surface of the container at a position slightly above the interface between the separated light and heavy phases.

2. The separator of claim 1 wherein the sealant is a silicone grease.

3. The separator of claim 1 which additionally comprises a closure adapted to seal the open end of the container after the blood has been separated and said barrier assembly inserted in said tubular container.

4. The separator of claim 3 wherein said closure is formed from an elastomeric material.

5. The separator of claim 1 wherein said average specific gravity is 1.06.

* * * * *